(12) United States Patent
Lee et al.

(10) Patent No.: US 7,662,064 B2
(45) Date of Patent: Feb. 16, 2010

(54) PERSONAL TRAINING DEVICE USING GPS DATA

(75) Inventors: Wai C. Lee, Olathe, KS (US); Tracy L. Oliver, Olathe, KS (US); Ryan T. Moore, Overland Park, KS (US); Claudette D. Fisher, McMinnville, OR (US); David J. Downey, Louisburg, KS (US); John H. Lovitt, Spring Hill, KS (US); Scott J. Brunk, Overland Park, KS (US)

(73) Assignee: Garmin Ltd (KY)

( * ) Notice: Subject to any disclaimer, the term of this patent is extended or adjusted under 35 U.S.C. 154(b) by 5 days.

(21) Appl. No.: 11/956,175

(22) Filed: Dec. 13, 2007

(65) Prior Publication Data

US 2008/0096727 A1 Apr. 24, 2008

Related U.S. Application Data

(60) Division of application No. 10/993,175, filed on Nov. 19, 2004, which is a continuation of application No. 10/462,968, filed on Jun. 17, 2003, now Pat. No. 6,837,827.

(51) Int. Cl.
*A63B 71/00* (2006.01)
(52) U.S. Cl. .................................. 482/8; 482/3; 482/900
(58) Field of Classification Search ................. 482/1–9, 482/900–902; 342/357.06, 357.17; 340/539.13
See application file for complete search history.

(56) References Cited

U.S. PATENT DOCUMENTS

| | | | |
|---|---|---|---|
| 4,408,613 A | 10/1983 | Relyea | 600/483 |
| 5,148,002 A | 9/1992 | Kuo et al. | |
| 5,406,491 A | 4/1995 | Lima | |
| 5,476,427 A | 12/1995 | Fujima | 482/3 |
| 5,552,989 A | 9/1996 | Bertrand | 701/200 |
| 5,583,776 A | 12/1996 | Levi et al. | 364/450 |
| 5,667,459 A | 9/1997 | Su | 482/4 |
| 5,687,136 A | 11/1997 | Borenstein | |
| 5,902,214 A | 5/1999 | Makikawa et al. | 482/4 |
| 5,921,891 A | 7/1999 | Browne | 482/8 |
| 6,002,982 A | 12/1999 | Fry | 701/213 |
| 6,009,138 A | 12/1999 | Slusky | 377/5 |
| 6,013,007 A | 1/2000 | Root et al. | 482/8 |
| 6,024,655 A | 2/2000 | Coffee | |
| 6,032,108 A | 2/2000 | Seiple et al. | 702/97 |

(Continued)

OTHER PUBLICATIONS

Office Action dated Jun. 3, 2008 from U.S. Appl. No. 11/208,819, filed Aug. 22, 2005.

(Continued)

*Primary Examiner*—Glenn Richman
(74) *Attorney, Agent, or Firm*—Samuel M. Korte

(57) ABSTRACT

A personal training device (10) adapted to assist a user in reaching performance goals, navigating, and accumulating performance statistics. In a preferred embodiment, the device broadly comprises a housing (10); an attachment mechanism (30); a GPS component (40); a user interface (50), including an input portion (52) and an output portion (54); a processor (60), including a timer (62) and a memory element (64); a data interface (70), including an input portion (72) and an output portion (74); an audio component (80); and a power supply (90). The device (10) is adapted to store goal information, monitor performance using GPS-derived data, and communicate performance information.

10 Claims, 8 Drawing Sheets

U.S. PATENT DOCUMENTS

| | | | |
|---|---|---|---|
| 6,050,924 A | 4/2000 | Shea | 482/8 |
| 6,064,942 A | 5/2000 | Johnson et al. | |
| 6,066,075 A | 5/2000 | Poulton | 482/8 |
| 6,067,046 A | 5/2000 | Nichols | |
| 6,122,960 A | 9/2000 | Hutchings et al. | 73/493 |
| 6,132,391 A | 10/2000 | Onari et al. | 600/595 |
| 6,148,262 A | 11/2000 | Fry | 701/213 |
| 6,152,856 A | 11/2000 | Studor et al. | 482/8 |
| 6,167,346 A | 12/2000 | Fukawa | 701/208 |
| 6,182,010 B1 | 1/2001 | Berstis | |
| 6,244,987 B1 | 6/2001 | Ohsuga et al. | 482/4 |
| 6,251,048 B1 | 6/2001 | Kaufman | 482/8 |
| 6,305,221 B1 | 10/2001 | Hutchings | 73/488 |
| 6,336,891 B1 | 1/2002 | Fedrigon et al. | 482/8 |
| 6,339,746 B1 | 1/2002 | Sugiyama et al. | 701/209 |
| 6,359,837 B1 | 3/2002 | Tsukamoto | 368/10 |
| 6,366,855 B1 | 4/2002 | Reilly et al. | 701/213 |
| 6,426,719 B1 | 7/2002 | Nagareda et al. | 342/357.06 |
| 6,428,449 B1 | 8/2002 | Apseloff | 482/3 |
| 6,446,005 B1 | 9/2002 | Bingeman et al. | |
| 6,449,583 B1 | 9/2002 | Sakumoto et al. | 482/8 |
| 6,450,922 B1 | 9/2002 | Henderson et al. | 482/8 |
| 6,463,385 B1 | 10/2002 | Fry | 701/213 |
| 6,466,232 B1 | 10/2002 | Newell et al. | 345/700 |
| 6,498,994 B2 | 12/2002 | Vock et al. | |
| 6,510,379 B1 | 1/2003 | Hasegawa et al. | 701/202 |
| 6,513,046 B1 | 1/2003 | Abbott, III et al. | 707/104.1 |
| 6,513,532 B2 | 2/2003 | Mault | 128/921 |
| 6,532,432 B1 | 3/2003 | Nagatsuma et al. | 702/149 |
| 6,539,336 B1 | 3/2003 | Vock et al. | |
| 6,546,336 B1 | 4/2003 | Matsuoka et al. | 701/213 |
| 6,549,845 B2 | 4/2003 | Eakle, Jr. et al. | 701/207 |
| 6,549,915 B2 | 4/2003 | Abbott, III et al. | 707/104.1 |
| 6,570,532 B2 | 5/2003 | Mise et al. | 342/357.1 |
| 6,571,200 B1 | 5/2003 | Mault | 702/182 |
| 6,572,511 B1 | 6/2003 | Volpe | 482/4 |
| 6,582,342 B2 | 6/2003 | Kaufman | 482/8 |
| 6,594,617 B2 | 7/2003 | Scherzinger | |
| 6,621,423 B1 | 9/2003 | Cooper et al. | 340/995.24 |
| 6,702,719 B1 | 3/2004 | Brown et al. | 482/8 |
| 6,740,007 B2 | 5/2004 | Gordon et al. | 482/8 |
| 6,744,403 B2 | 6/2004 | Milnes et al. | 342/357.07 |
| 6,746,371 B1 | 6/2004 | Brown et al. | 482/8 |
| 6,837,827 B1 | 1/2005 | Lee et al. | 482/8 |
| 6,853,955 B1 | 2/2005 | Burrell | 702/182 |
| 7,057,551 B1 | 6/2006 | Vogt | 342/357.06 |
| 2002/0046692 A1 | 4/2002 | Pharo et al. | 116/200 |
| 2004/0046692 A1 | 3/2004 | Robson et al. | 482/8 |

OTHER PUBLICATIONS

U.S. Appl. No. 10/786,377, Burrell et al.

```
     DAYS              LAPS
   ┌────────────────────────┐
   │ APR03  12:20pm       2 │
   └────────────────────────┘

00:24:25           2.49mi
   09:48/mi           295Cal
```

*Fig. 16.*

```
     WEEKS             LAPS
   ┌────────────────────────┐
   │ MAR30 - APR05        2 │
   └────────────────────────┘

00:24:25           2.49mi
   09:48/mi           295Cal
```

*Fig. 17.*

```
   LAPS
   ┌────────────────────────┐
   │ LAP 1          12:20pm │
   └────────────────────────┘
     LAP 2          12:43pm

00:22:18           2.27mi
   09:49/mi           269Cal
```

*Fig. 18.*

PERSONAL TRAINING DEVICE USING GPS DATA

RELATED APPLICATIONS

This present application is a divisional application and claims priority benefit of U.S. patent application Ser. No. 10/993,175, filed Nov. 19, 2004, entitled PERSONAL TRAINING DEVICE USING GPS DATA, which in turn is a continuation application and claims priority benefit to U.S. patent application Ser. No. 10/462,968, filed Jun. 17, 2003, now U.S. Pat. No. 6,837,827, entitled PERSONAL TRAINING DEVICE USING GPS DATA. Each of the above-identified applications is incorporated into the present application by reference.

BACKGROUND

1. Field of the Invention

The present invention relates broadly to devices using Global Positioning System (GPS) data to facilitate physical training. More particularly, the present invention concerns a physical training device using GPS data to assist a user in reaching performance goals and completing training sessions by tracking user performance; communicating progress, including progress relative to user-defined goals; communicating navigation directions and waypoints; and storing and analyzing training session statistics.

2. Description of Prior Art

Many people who exercise strive to improve their performance. A runner or a bicyclist, for example, may desire to improve performance by increasing speed over a defined distance or by increasing total distance that can be traveled without resting.

One well-known method exercisers may use to improve performance is to set and strive to reach performance goals. This requires that the exerciser measure performance during the training session and compare the measured performance to the pre-defined goals. For example, if an exerciser desires to increase his or her average running speed, he or she would set an average speed goal, measure an actual average speed during a training session, and then compare the average speed goal with the actual average speed. In this manner, the exerciser is provided with performance feedback that can be used as a guide for future training sessions.

To measure actual average speed, an exerciser typically measures an elapsed time of the training session using a stopwatch, measures the distance traveled during the session using a map or landmarks, and divides the distance traveled by the elapsed time. Unfortunately, this requires that the exerciser carry the stopwatch and remember to start and stop the stopwatch at appropriate points during the training session. It also requires that the exerciser determine the distance traveled. If the exerciser uses a non-standard or arbitrarily-defined course, the distance can sometimes be roughly determined from a vehicle's odometer, though the result may be significantly inaccurate. Where the course cannot be driven with a vehicle, such as, for example, where the course is over open country or over water, some other means of determining distance must be devised. Pedometers, for example, are known in the prior art for measuring distance traveled. Unfortunately, pedometers suffer from a number of disadvantages, including, for example, that they must be properly calibrated; are inaccurate for most forms of movement other than running; and the runner must maintain consistent strides regardless of such factors as changing terrain. Following an arbitrary course can also make repeating the course extremely difficult because the exerciser may not recall the course's exact route. Furthermore, this method makes it very difficult for the user to be aware of performance and progress toward reaching the pre-defined goals during the training session.

The prior art methods of measuring performance also make it very difficult to use goals in interval training, a training system wherein an exerciser strives to achieve different performance characteristics during different intervals of the training session. Using the traditional approach of measuring performance, an exerciser must recognize or be made aware of the completion of one interval and the beginning of the next, and must stop measuring performance characteristics of the completed interval and begin measuring performance characteristics of the next interval. Although many training devices offer a manual "lap memory" feature to facilitate recording performance characteristics for multiple intervals of a training session, use of these devices is cumbersome. Using the manual lap memory feature in time-based interval training, for example, exercisers must constantly compare an interval goal with the time on a stopwatch and manually trigger lap recording upon completion of each interval. Using the manual feature with distance-based and speed-based interval training is further complicated because the user must accurately determine a distance traveled or a current speed, which is difficult or impossible in some situations as discussed above. Thus, the traditional methods associated with measuring performance are cumbersome, restrictive, and are not practical or useful for some types of training sessions.

People who exercise also often desire to accumulate performance information overtime. An exerciser may, for example, perform a historical or statistical analysis of the performance information gathered over a week or a month. Typically, accumulating performance information involves the laborious process of manually recording the performance characteristics for each training session over the desired period of time. Furthermore, the exerciser may be restricted to exercising on a particular closed course for extended periods of time in order to consistently record accurate performance information, such as, for example, distance.

Accumulating performance information becomes more difficult if the exerciser performs two or more types of exercise during one training session and desires to maintain the performance information from each type of exercise separately. For example, an exerciser may walk during part of a training session and run during another part of the same training session and desire to accumulate running statistics separately from walking statistics. Traditionally, this would require the exerciser to be aware of transitions from one type of exercise to another and be able to record session information such as, for example, distance, for each type of exercise. This may be difficult or even impossible if the exerciser wishes to arbitrarily transition from one type of exercise to another such as, for example, transitioning from a run to a walk whenever the exerciser becomes tired.

In addition to the challenges associated with accumulating performance data, calculating historical and statistical analyses on the performance data presents a further challenge. A computer is often needed to perform the analyses quickly and efficiently, which requires the user to have a computer at the exercise site or leave the exercise site in order to access a computer to view the analyses. Furthermore, if the user does not have an exercise device adapted to automatically store performance data in a manner in which it can be transferred to a computer, the user has the burden of manually entering the data into the computer.

Due to the above-mentioned and other problems and disadvantages in the art, a need exists for an improved mechanism to assist a user in reaching performance goals, navigating during a training session, and recording and analyzing training session statistics.

SUMMARY

The present invention overcomes the above-described and other problems and disadvantages in the prior art with a personal training device adapted to assist a user in reaching performance goals and completing training sessions by tracking user performance; communicating progress, including progress relative to user-defined goals; communicating navigation directions and waypoints; and storing and analyzing training session statistics. The device may be used, for example, by an exerciser or other user on a well-defined course or on an undefined course, for land-based activities or water-based activities, and for any combination thereof. In a preferred embodiment, the device broadly comprises a GPS component; a user interface, including an input portion and an output portion; a processor, including a timer and a memory element; a data interface, including an input portion and an output portion; an audio component; a power supply; a housing for enclosing the aforementioned components and an attachment mechanism for associating the housing with the user.

The GPS component provides, in a conventional manner, geographic location information based on signals received from two or more members of an array of orbiting satellites. The GPS component may be, for example, a GPS receiver much like those provided in products by Garmin Corporation.

The user interface allows the user to provide input to the processor via the input portion of the user interface, and to allow the processor to communicate with the user via the output portion of the interface. The processor receives and processes information from the GPS component, from the input portion of the user interface, and from the input portion of the data interface and provides information via the output portion of the user interface and the output portion of the data interface.

The timer is used for monitoring time and the memory element is used to store information. The data interface allows a user to transfer information to or from a computing device. The audio component provides audible training information. The power supply provides power to the various other components of the device.

The housing contains or encloses the remaining components so as to protect and shield them from the hazards of use and of the environment. The housing may take any suitable shape, including, for example, ergonomic shapes molded to substantially correspond to a portion of the user's body whereupon or against which the housing is meant to rest. The attachment mechanism secures, retains, or maintains the housing in close physical association with the user. As such, the attachment mechanism may take the form of any mechanism suitable to such functionality. The attachment mechanism may also provide for adjustment and for elastically accommodating the user's movement and flexibility.

Broadly, the device uses information from the GPS component, the input portion of the user interface and the input portion of the data interface to advantageously assist the user in accomplishing at least three tasks, including reaching a performance goal, navigating, and accumulating statistics.

It will be appreciated that the device of the present invention provides a number of substantial advantages over the prior art, including, for example, automatically tracking user performance, thereby eliminating the need for the user to manually measure performance during a training session or follow a predetermined course. Furthermore, the device communicates goal and performance information to the user, helping the user reach pre-defined goals during the training session by informing the user of progress toward the goals. Additionally, the device automatically accumulates and stores performance statistics, eliminating the need for the user to manually record performance information and maintain the information for extended periods of time. Additionally, the device communicates GPS-based navigation information to the user, enabling the user to visually monitor his or her location on a map or position on a course.

These and other important features of the present invention are more fully described in the section titled DETAILED DESCRIPTION OF PREFERRED EMBODIMENTS, below.

BRIEF DESCRIPTION OF THE DRAWINGS

Preferred embodiments of the present invention are described in detail below with reference to the attached drawing figures, wherein:

FIG. 16 is a depiction of a third visual graphic adapted for use in completing a third task of assisting a user in accumulating and analyzing performance statistics;

FIG. 17 is a depiction of a fourth visual graphic adapted for use in completing a third task of assisting a user in accumulating and analyzing performance statistics; and FIG. 18 is a depiction of a fifth visual graphic adapted for use in completing a third task of assisting a user in accumulating and analyzing performance statistics.

DETAILED DESCRIPTION

Figure 1:
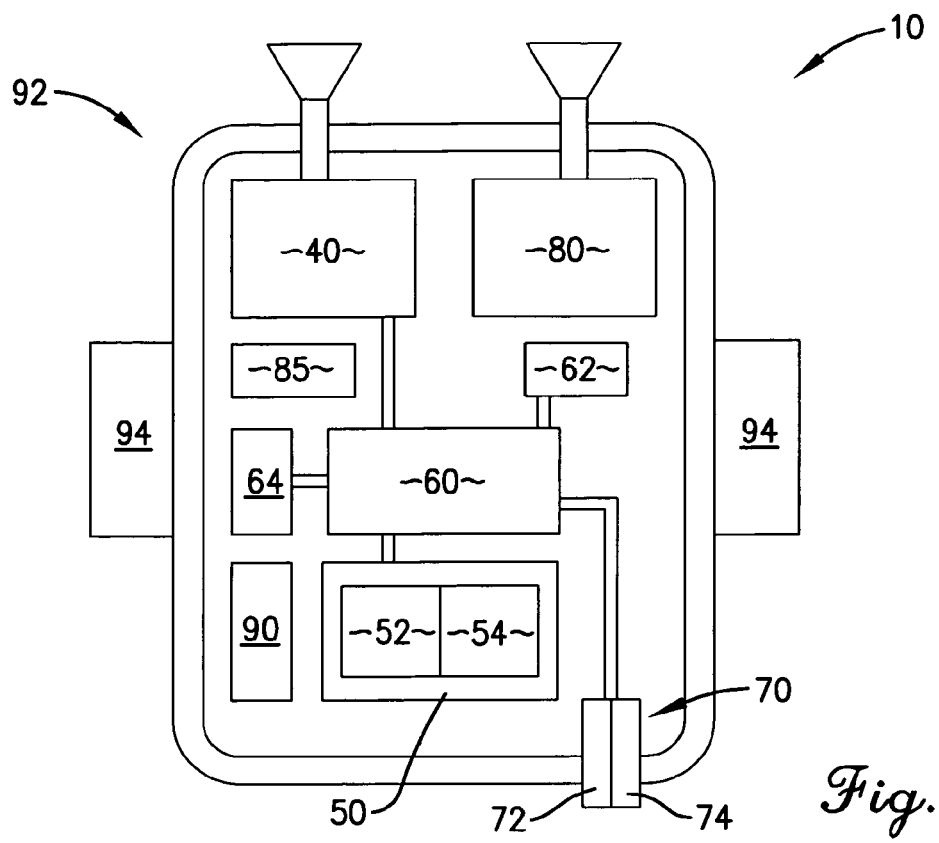
FIG. 1 is a schematic of components in a preferred embodiment of the personal training device of the present invention.

Referring to FIG. 1, a personal training device 10 is shown constructed in accordance with a preferred embodiment of the present invention. The device 10 is adapted to assist a user in reaching performance goals and completing training sessions by tracking user performance; communicating progress, including progress relative to user-defined goals; communicating navigation directions and waypoints; and calculating and storing training session statistics. The device 10 may be used, for example, by an exerciser or other user on a well-defined course or on an undefined course, for land-based activities or water-based activities, or for any combination thereof.

In the illustrated preferred embodiment, the device 10 broadly comprises a GPS component 40; a user interface 50, including an input portion 52 and an output portion 54; a processor 60, including a timer 62 and a memory element 64; a data interface 70, including an input portion 72 and an output portion 74; an audio component 80; a power supply 90; a housing 92; and an attachment mechanism 94.

The GPS component 40 is adapted to provide, in a substantially conventional manner, geographic location information for the device 10 based on signals received from two or more members of an array of orbiting satellites. This location information is provided to the processor 60. The GPS component may be, for example, a GPS receiver much like those provided in products by Garmin Corporation.

Figure 2:
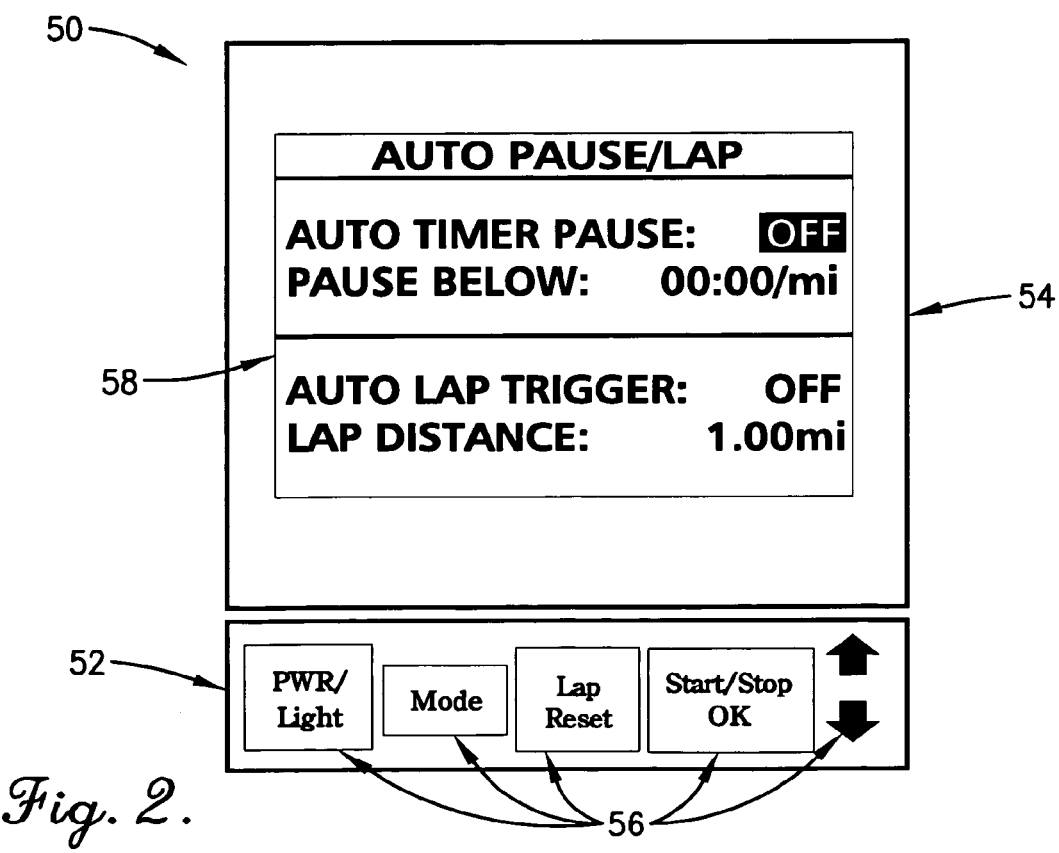
FIG. 2 is a plan view of an interface component of the device of FIG. 1.

Referring also to FIG. 2, the user interface 50 is adapted to receive a user input and to communicate the input to the processor 60 via the input portion 52 of the user interface 50, and to allow the processor to communicate an output via the output portion 54 of the interface 50. The input portion 52 preferably includes one or more buttons, switches, membraneous keypads, or other input mechanisms 56 for providing input to the processor 60. Such input may include, for example, a PWR/Light input to turn the unit on and off and to turn a back light on and off; a Mode input to change an operating mode of the unit; a Lap/Reset input to trigger a lap or to reset a timing function; a Start/Stop/OK input to start and stop the timing function or to confirm a menu selection; and up and down inputs to choose a data screen or change selections within a data screen. The output portion 54 preferably includes a visual display 58, such as, for example, an LCD screen, for visually communicating information, such as, for example, total distance, total distance goal, speed, and speed goal. The visual display 58 is adapted to display information using large font and images for easy reference during a training session, using small font and images to accommodate more information while the user is reviewing performance characteristics or programming the device 10, or using a combination of large and small font and images.

The data interface 70 is adapted to allow a user to transfer information to a computing or sensing device using the output portion 74 or from a computing or sensing device using the input portion 72. The data interface 70 may be, used, for example, for downloading monitored and stored performance data from the device 10 to a personal computer for later reference or additional processing (e.g., graphing over time).

The processor 60 is adapted to receive and process information from the GPS component 40, from the input portion 52 of the user interface 50, and from the input portion 72 of the data interface 70. The processor 60 is adapted to communicate information via the output portion 54 of the user interface 50 and the output portion 74 of the data interface 70. The timer 62 is adapted to monitor time, much like a stopwatch, and to calculate speed, as described below. The memory element 64 is used to store information, including, for example, the number of laps completed, geographical locations, total time, total distance, and average speed. The audio component 80 is adapted to provide audible training information such as, for example, calculated or monitored performance characteristics and goals. The audio component 80 gives voice to electronic output signals generated by the processor 60 and may comprise, for example, a speaker and an earphone jack.

The processor 60 may be provided with an altimeter 85 to provide altitude information to the processor 60. The processor may use the altitude information when calculating, for example, an elevation or a change in elevation which could affect the user's performance.

The power supply 90 provides power to the various other components of the device 10. Preferably the power supply 90 is in the form of a battery, whether rechargeable or non-rechargeable.

The housing 92 is adapted to enclose and contain other components of the device 10 so as to protect and shield them from the hazards of use (e.g., jostling, dropping, other mechanical shock) and of the environment (e.g., rain, dust). As such, the housing 92 is preferably constructed from a suitable lightweight and impact-resistant material such as, for example, plastic, nylon, aluminum, or any combination thereof. Additionally, the housing 92 preferably includes one or more appropriate gaskets or seals 96 to make it substantially waterproof or resistant. Though shown as being substantially rectangular, the housing 92 may take any suitable shape, including, for example, ergonomic shapes molded to substantially correspond to a portion of the user's body (e.g., arm, leg, hip) whereupon or against which the housing 92 is meant to rest.

The attachment mechanism 94 is adapted to secure, retain, and maintain the housing 92 in close physical association with the user. As such, the attachment mechanism 94 may take the form of any mechanism suitable to such functionality, including, for example, an armband-type mechanism for securing the housing 92 to the user's arm; a waistband-type mechanism for securing the housing 92 to the user's waist; a belt hook-type mechanism for securing the housing 92 to the user's belt or waistband; or an over-the-shoulder-type mechanism for wearing the housing 92 over the user's shoulder. Furthermore, the attachment mechanism 94 is preferably adjustable using, for example, a conventional buckle or hook-and-loop-type mechanism. Additionally, the attachment mechanism 94 is, when appropriate, preferably elastic or otherwise accommodating of the user's movement and flexibility.

The device 10 uses information from the GPS component 40, the input portion 52 of the user interface 50, and the input portion 72 of the data interface 70 to assist the user in accomplishing at least three tasks, including a first task of reaching a performance goal, a second task of navigating, and a third task of accumulating and analyzing statistics. Each of these tasks, and how they are enabled with the present invention, are described below.

The device 10 may assist the user in accomplishing the first task of reaching performance goals by automatically monitoring and reporting the user's performance. The device 10 may monitor the user's performance by using the processor 60 to calculate and track any of a variety of performance characteristics, such as, for example, the user's location, elevation, distance, elapsed time, speed or calories burned. For example, the processor 60 may calculate a location by using location data from the GPS component 40. The processor 60 may calculate an elevation using location data from the GPS component 40, altitude information from the altimeter 85, or both. The processor 60 may calculate a change in elevation by comparing a current elevation with a previous elevation. The processor 60 may calculate a distance by comparing a current location with a previous location. The processor 60 may calculate an elapsed time using data from the timer 62 by comparing a previous time with a current time. The processor 60 may calculate a speed by comparing a distance with an elapsed time. The processor 60 may calculate a number of calories burned based upon the user's current speed and the user's body weight, and may also consider distance and change in elevation.

Figure 3:
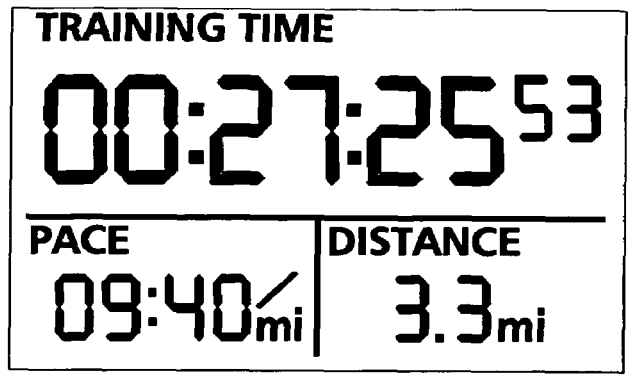
FIG. 3 is a depiction of a first visual graphic performance indicator adapted for use in completing a first task of assisting a user to reach performance goals.
Figure 4:
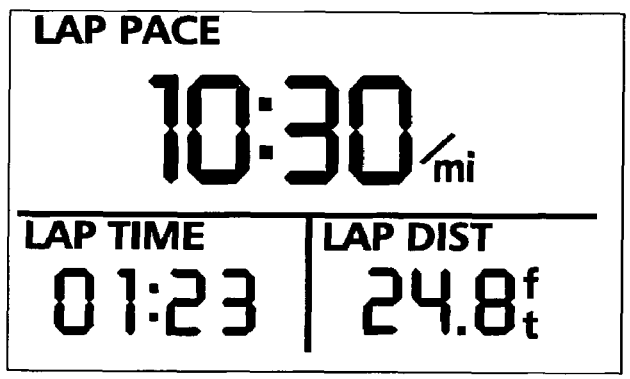
FIG. 4 is a depiction of a second visual graphic performance indicator adapted for use in completing a first task of assisting a user to reach performance goals.
Figure 5:
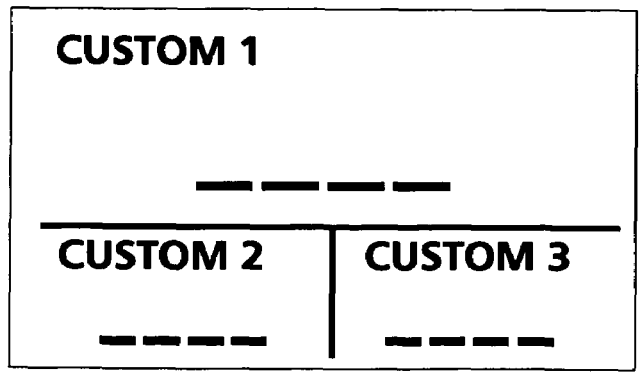
FIG. 5 is a depiction of a third visual graphic performance indicator adapted for use in completing a first task of assisting a user to reach performance goals.

The user may choose the performance characteristics to display on the user interface 50, either using default data screens such as those depicted in FIG. 3 and FIG. 4, or by creating a customized data screen, depicted in FIG. 5. The device 10 is adapted to allow users to switch between various modes of monitoring and reporting performance characteristics by pressing a button. Automatically monitoring and reporting the user's performance would be a convenient and sufficient method of assisting the user in reaching performance goals in situations where the user can easily remember the performance goal and measure progress towards reaching the goal, such as, for example, when striving to reach a time goal or a distance goal while running on a closed track. For situations in which remembering performance goals and measuring progress may be difficult or impossible, the device 10 is also adapted to record goals, automatically measure progress towards reaching those goals, and report the progress to the user.

Figure 6:
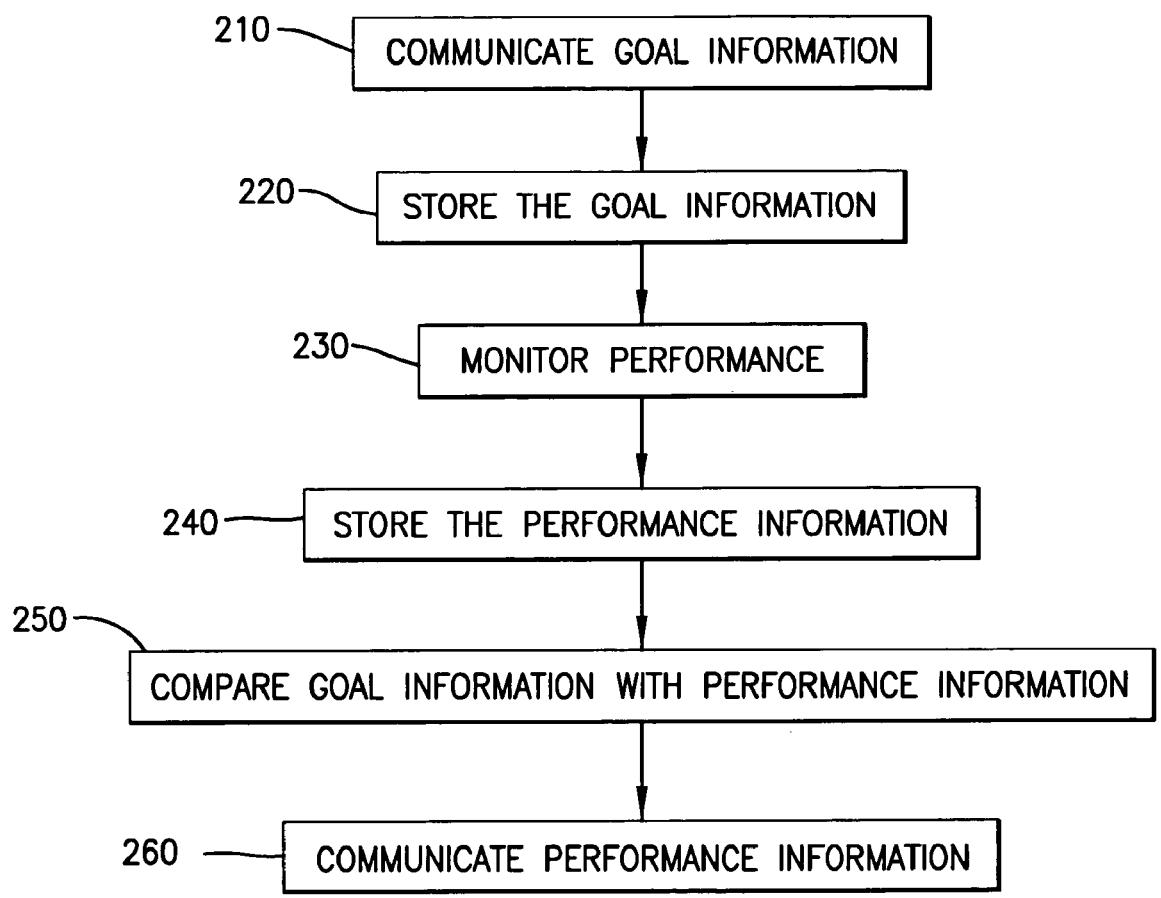
FIG. 6 is a flowchart of steps involved in completing a first task of assisting a user to reach performance goals.
Figure 7:
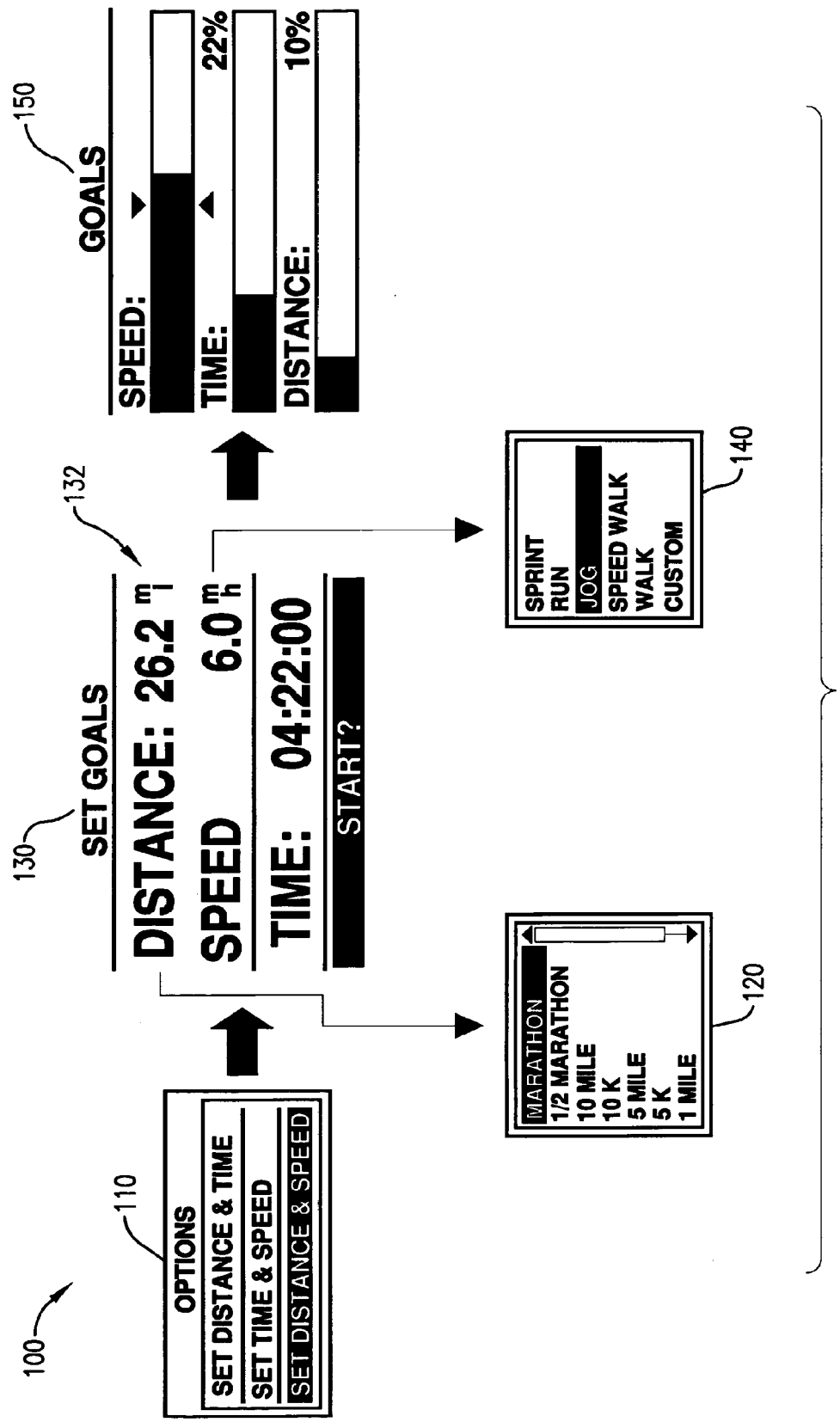
FIG. 7 is a block diagram of visual graphic menus adapted for use in completing the task of FIG. 6.
Figure 8:
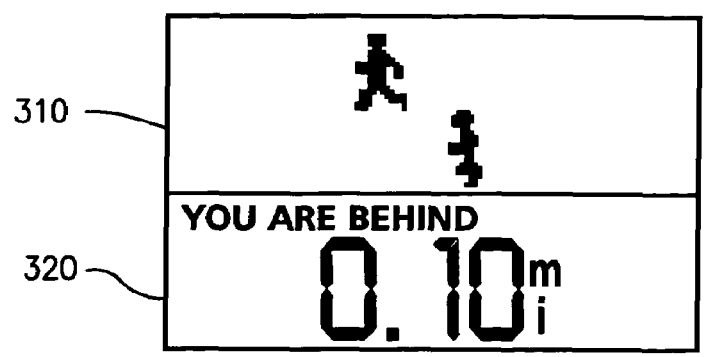
FIG. 8 is a depiction of a fourth visual graphic performance indicator adapted for use in completing the task of FIG. 6.
Figure 9:
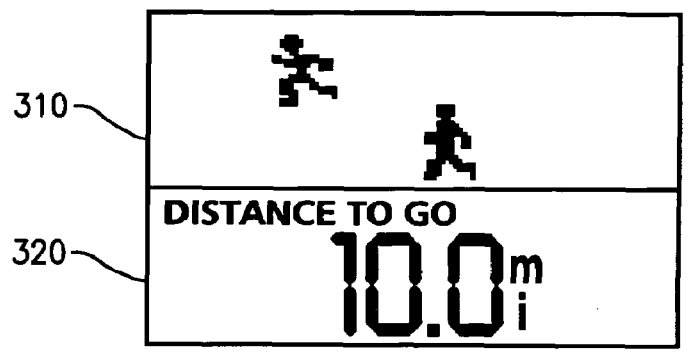
FIG. 9 is a depiction of a fifth visual graphic performance indicator adapted for use in completing the task of FIG. 6.
Figure 10:
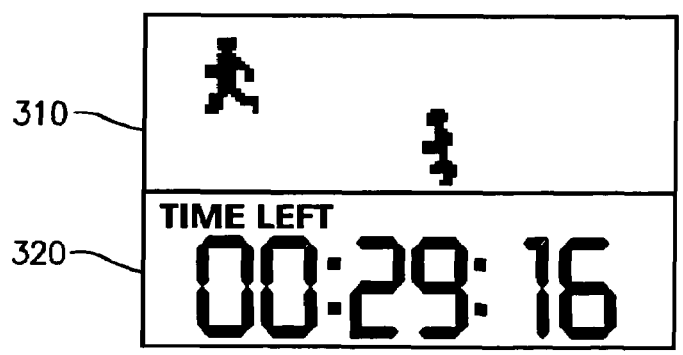
FIG. 10 is a depiction of a fourth visual graphic performance indicator adapted for use in completing the task of FIG. 6.
Figure 11:
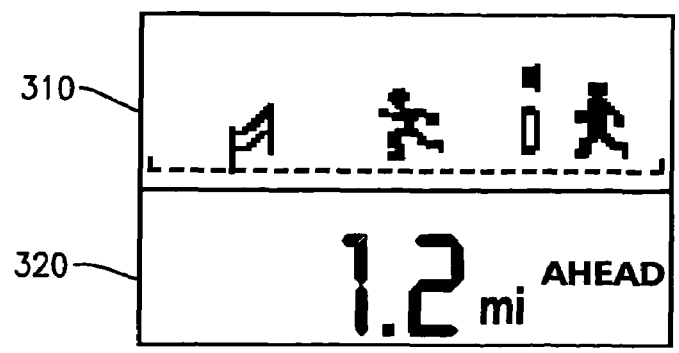
FIG. 11 is a depiction of a fourth visual graphic performance indicator adapted for use in completing the task of FIG. 6.

Referring to FIG. 6 and FIG. 7, the device 10 may also assist the user in accomplishing the first task of reaching a performance goal by first allowing the user to communicate goal information to the processor 60, as depicted in block 210. The goal information may relate to, for example, average speed, maximum speed, distance, or time for one or more training intervals or for an entire training session. The user may manually communicate the goal information to the processor 60 via the input portion 52 of the user interface 50, may download goal information from an external device to the processor 60 by connecting the external device to the input portion 72 of the data interface 70, and may use goal information stored in the memory element 64. The processor 60 stores the goal information in the memory element 64, as depicted in block 220.

The device 10 then monitors the user's performance, as depicted in block 230, by using the processor 60 to calculate and track any of a variety of performance characteristics, as described above. The processor 60 preferably stores the performance information in the memory element 64, as depicted in block 240.

The processor 60 uses the goal information and the performance information to assist the user in reaching the pre-defined goals, such as, for example, by comparing the goal information with the performance information, as depicted in block 250, and communicating performance information relative to goal information, as depicted in block 260. The device 10 may communicate with the user via the output portion 54 of the user interface 50, the audio component 80 or the output portion 74 of the data interface 70.

It will be appreciated that the above-described mechanism for assisting a user in reaching performance goals may be used in a variety of activities, sports, and types of training. For example, the device 10 is preferably adapted to assist the user in interval training by recognizing various segments of a training lap or course and allowing the user to program particular goals for each of the segments. The device 10 may notify the user of a transition from one segment to another and assist the user in reaching the particular goals related to each segment.

In a first preferred implementation, the user communicates performance goal information to the processor 60 via the input portion 52 of the user interface 50. The processor 60 visually guides the user through the process of setting goals with a menu sequence 100 shown on the display 58. The menu sequence 100 may include an options menu 110 which allows the user to choose the performance goal or goals he wishes to set, and a goal screen 130 which shows a current goal value 132. The goal screen 130 allows the user to change the goal value 132 by using goal value menus 120, 140 with commonly use pre-defined goal values, or by communicating arbitrary goal information to the processor 60 via the input portion 52 of the user interface 50. The user presses a start button 56 on the user interface 50 to begin the training session.

The device 10 preferably motivates the user to reach his or her performance goals at various times, including during a training session and after a training session. During a training session the device 10 may motivate the user to reach the performance goal by, for example, instructing the user to modify performance, encouraging the user to maintain the performance, and alerting the user when a goal has been reached. The device 10 may instruct the user to modify performance by, for example, showing progress bars 150 on the display 58 which reflect the user's progress toward reaching the goals, or by sending an audio message to the audio component 80 such as, for example, "increase your speed by five percent" or "you are fifty feet behind schedule." After a training session, the virtual coach may motivate the user to reach the goals by, for example, congratulating the user for partially reaching a goal and suggesting a new goal; scolding the user for not reaching a goal; encouraging the user to try again; or recommending improvement strategies based upon the user's performance. The device 10 may communicate with the user constantly or only at particular times, places, or intervals. For example, it may communicate with the user only at specified lap markers to simulate a coach standing at a point on a track and speaking to the user as he or she passes the coach. The device 10 preferably has two or more personalities for the user to choose from, including, for example, male and female, passive and active, less aggressive and more aggressive.

Referring also to FIGS. 8-11, in a second preferred implementation, the device 10 is adapted to create a virtual competitor to compete against the user by using a performance profile of a virtual athlete who achieves the user's goals and informing the user of his or her performance relative to the virtual athlete. The device 10 may inform the user by, for example, communicating via the display 58 a graphic 310 of the user's position relative to the virtual competitor, displaying a text message 320 indicating the user's position relative to the virtual competitor or other performance information, or both. The device 10 may also inform the user with an audio message using the audio component 80. For example, if the training session includes running, the device 10 may show a graphic of a race on the display 58, in which the position of both the user and the competitor are visible, and may play an audio depiction of the competitor's footsteps as the competitor gets closer.

The virtual competitor may have a performance profile corresponding to the performance of an actual person, allowing the user to gauge his or her performance against other people. The performance profile of a person, such as, for example, a well-known or professional athlete, may be downloaded into the device via the input portion 74 of the data interface 70. In addition to downloading a performance profile, the device may create a performance profile of the user by gathering the user's performance characteristics during a training session and assembling the characteristics into a performance profile. This would allow the user, for example, to simulate training with a companion if the companion is absent by enabling the companion to create a performance profile in a previous training session and store the profile in the memory element 64 for later use. The device 10 preferably allows the user to compete against more than one virtual competitor at a time, including, for example, competitors with virtual performance profiles and competitors with performance profiles of actual people. The virtual competitor may take forms other than an athlete, such as, for example, a virtual chaser which runs behind or chases the runner and encourages him or her to meet performance goals.

Figure 12:
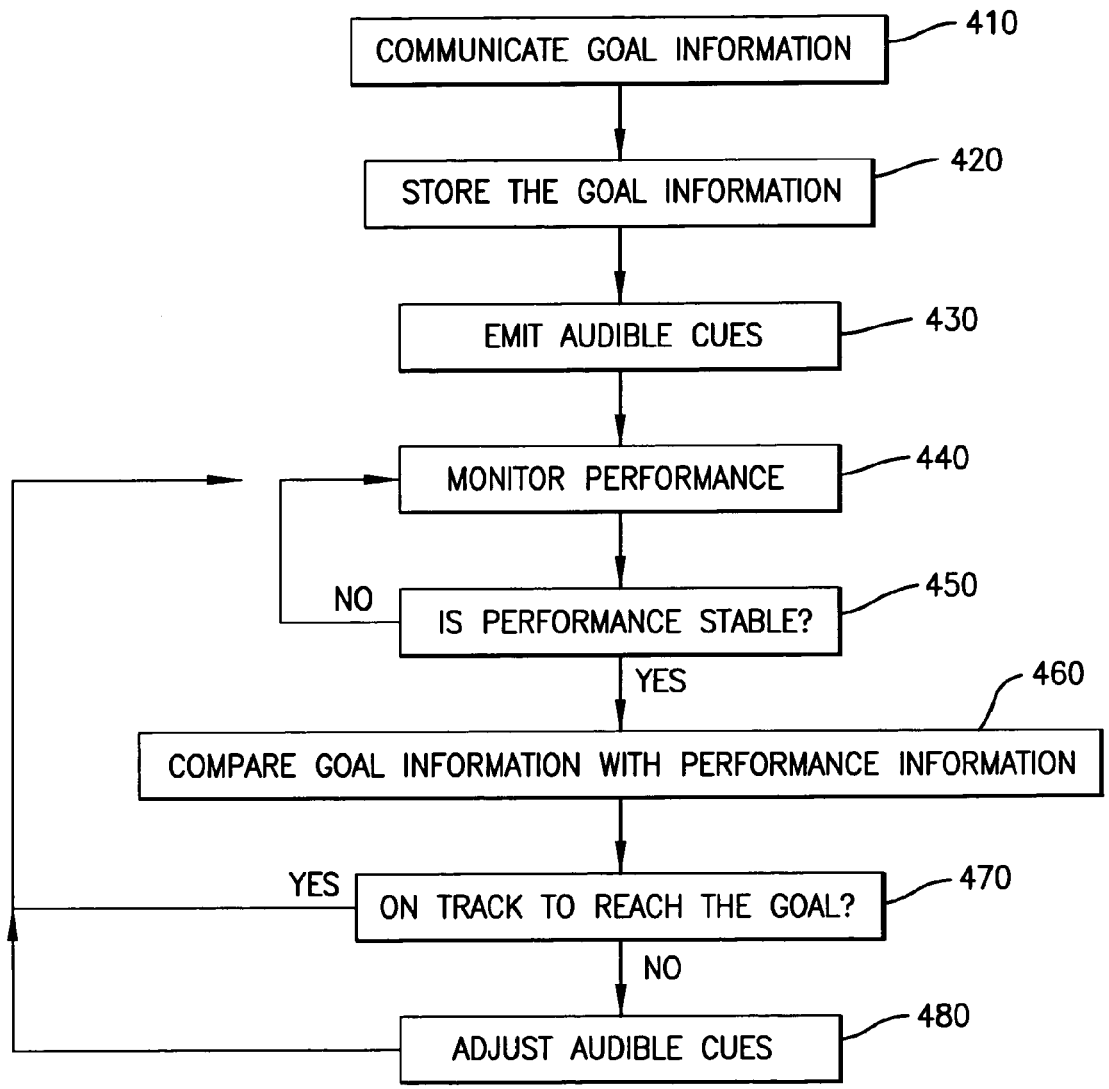
FIG. 12 is a flowchart of steps involved in completing a preferred implementation of the first task of assisting the user to reach performance goals.

Referring also to FIG. 12, in a third preferred implementation, the user communicates performance goal information to the processor 60 via the input portion 52 of the user interface 50, as depicted in block 410. The processor 60 stores the goal information in the memory element 46, as depicted in block 420. The device 10 then assists the user in reaching a constant pace by emitting audible cues at a particular frequency, as depicted in block 430. The audible cues may be, for example, beeps emitted at one-second intervals, or music with a steady beat. The audible cues assist the user in reaching and maintaining a constant pace by allowing the user to match an exercise rhythm with the frequency of the audible cues. For example, a runner may take two steps per audible cue. The device 10 emits the audible cues via the audio component 80, the output portion 54 of the user interface 50, or both. The device 10 then monitors performance, as depicted in block 440. The device 10 may monitor performance using geographic location information and timing information. Speed is determined based upon GPS readings, and the number of strides per cue is calculated based upon speed and stride length. The device 10 then determines if the performance is stable, as depicted in block 450, by comparing a current performance characteristic with previous performance characteristics. For example, the device 10 may determine that performance has stabilized if a current speed is the same as a speed measured thirty seconds prior to the current speed. If the performance is not stable, the device 10 continues to monitor performance and check for performance stability until it determines that the performance is stable.

When the performance is stable, the device 10 compares the goal information with the performance information, as depicted in block 460, to determine if the performance goals have been met, as depicted in block 470. If the performance goal has not been met, the device 10 assists the user in reaching the goal by adjusting the frequency of the audible cues to reflect a change in performance needed to meet the goal. To help a user increase speed in order to reach a speed goal, for example, the device 10 gradually increases the frequency of the audible cues. If the user is on track to reach the goal the device 10 will assist the user in maintaining performance by maintaining the frequency of the audible cues. It will be appreciated that the device 10 can make use of audible tones in a variety of ways to assist the user in reaching performance goals, such as, for example, by emitting a certain tone if the user is going too fast and a different tone if the user is going too slow. Additionally, the device 10 may be adapted to enhance interval training by assisting the user in reaching pace-related goals during one or more intervals. For example, the device 10 may maintain a slow speed during a first interval, gradually increase the speed during a next interval to reach a higher speed, maintain the higher speed during a next interval, then gradually decrease the speed during a final interval.

Figure 13:
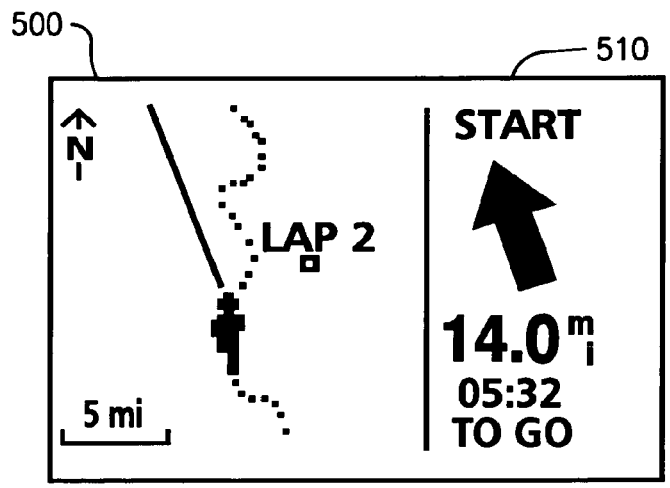
FIG. 13 is a depiction of a visual graphic adapted for use in completing a second task of assisting a user in navigating.

Referring also to FIG. 13, the device 10 may assist the user with the second task of navigating by first communicating location data from the GPS component 40 to the processor 60. The processor 60 then calculates user location information using the location data. The processor 60 communicates the location information to the user via the output portion 54 of the user interface 50 or the output portion 74 of the data interface 70. The processor 60 supplements the location information using map or course information stored in the memory element 64. The processor 60 preferably communicates the location information to the user by displaying a map of the user's location and placing a location marker 500 on the map indicating a position of the user on the map. The processor 60 may communicate the location information to the user in various ways including, for example, by visually or audibly communicating to the user a longitude and latitude.

The device 10 further assists the user in navigating by providing a preferred heading associated with a destination. The device 10 allows the user to manually store locations in the memory element 64, such as a starting location or a location of interest along a training route. The device 10 may also be adapted to automatically store locations in the memory element 64, such as by storing a starting location where the device 10 is turned on; where the device 10 begins or ends monitoring performance, such as when a timer function is started or stopped; where a training interval has been reached; or where a performance goal has been reached. The user can choose any of the stored locations and request the device 10 to provide navigation instructions 510 to return to the location. The navigation instructions 510 may include, for example, an arrow indicating a heading; a distance; and an estimated time of arrival based on a current speed and the distance.

It will be appreciated that the device 10 may use location and course information in various ways to assist the user in navigation. For example, the device 10 is preferably adapted to notify the user when the user has reached a predetermined point in a training session. The point may be a lap, distance, geographic location, elevation, time of day, elapsed time, or speed.

Figure 14:
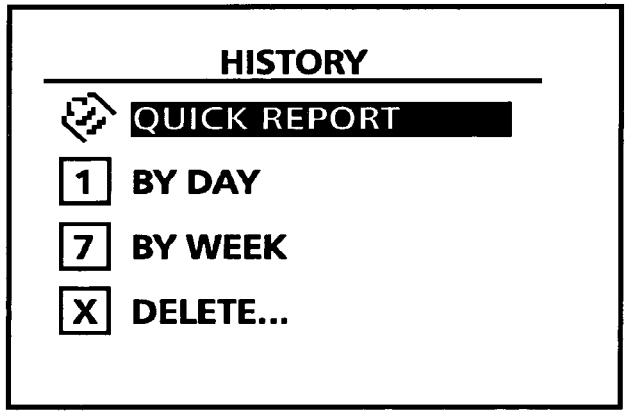
FIG. 14 is a depiction of a first visual graphic adapted for use in completing a third task of assisting a user in accumulating and analyzing performance statistics.
Figure 15:
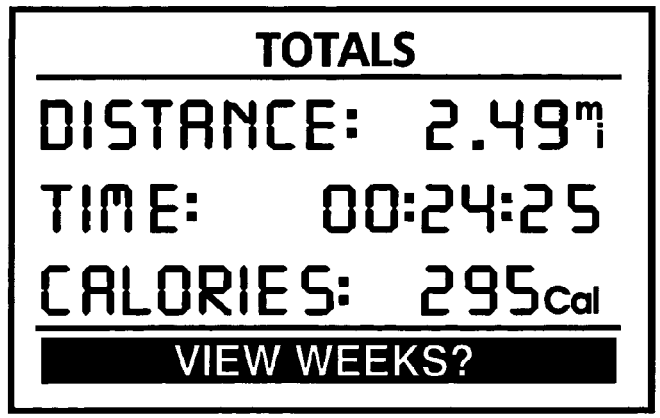
FIG. 15 is a depiction of a second visual graphic adapted for use in completing a third task of assisting a user in accumulating and analyzing performance statistics.

The device 10 may assist the user with the third task of accumulating and processing statistics by first monitoring the user's performance and storing performance characteristics in the memory element 64. The device 10 is preferably adapted to allow a user to select particular performance characteristics to monitor and store, and determine when the processor 60 will monitor and accumulate the characteristics. The processor 60 may perform a historical data analysis such as total distance traveled or total elapsed time of various training sessions. The processor 60 may also perform a statistical data analysis such as, for example, an average speed during a training session. The device 10 preferably allows the user to select from various time periods over which to perform the analyses, including, for example, a certain number of training sessions or a certain number of days. The device 10 is adapted to display a menu on the user interface 50 that allows a user to choose between several historical performance reports, as depicted in FIG. 14. The menu may include a "QUICK REPORT" function to allow a user to view a performance characteristic report of the prior exercise session. The menu may further include functions to allow the user to view performance characteristic reports covering the entire day, week, or longer. FIG. 15 illustrates an example of a quick report data screen. FIG. 16 and FIG. 17 illustrate examples of data screens corresponding to performance characteristic reports covering a day and a week, respectively.

The processor 60 is adapted to use performance information and user-defined performance thresholds to trigger the accumulation of training session statistics. A user may program a specific performance threshold over which the processor 60 will accumulate trip statistics. The threshold may be, for example, a speed of five miles per hour or an altitude of five thousand feet. Because the threshold is user-defined, the user may use this function for any of various sports that involve different performance characteristics, such as, for example, biking, jogging and walking. The device may use default performance thresholds for various sports, or may allow the user to program specific performance threshold values. In use the training processor 60 may calculate a current speed continuously throughout a trip and compare the speed to the threshold speed. When the current speed is above the threshold speed the processor 60 accumulates trip statistics. When the current speed is below the threshold speed the processor 60 does not accumulate trip statistics, or accumulates resting statistics rather than trip statistics. Thus, this function allows the user to discard resting statistics or distinguish between trip statistics and resting statistics.

The device 10 is further adapted to automatically record lap statistics, relieving the user of the burden of pressing a "LAP" button to record the statistics each time a lap is completed. The user may program the device 10 with lap indicators before a training session or during the session. For example, the user may define a lap as 400 meters so that the device records lap statistics at 400 meter intervals during the training session. The user may also program the device 10 to record lap statistics each time the user passes a location, such as a particular point on a circular track. Alternatively, the user may program or change the lap indicators during the training session by, for example, indicating the beginning and end of a lap and letting the device 10 calculate the distance traveled and assign that distance to a lap. Any time during a training session the user may view the performance characteristics associated with each lap, as depicted in FIG. 18.

The device 10 is further adapted to assist a user in interval training. The user may wish to pursue different goals during different portions, or intervals, of a training session. For example, the user may wish to separate a running training session into three one-mile intervals and assign a different time or average speed goal to each interval, or assign a time goal to one interval and an average speed goal to another interval. An interval need not be defined only by distance, but may be defined by any performance characteristic or combination of performance characteristics the device 10 is capable of monitoring, such as speed and distance. The device 10 is preferably adapted to communicate performance and goal information relative to an interval, and automatically store performance information at a given interval.

This functionality may be especially useful, for example, to an exerciser who is training for a triathlon, which is an athletic contest in which participants compete without stopping in three successive events, usually long-distance swimming, bicycling, and running. The average speed during the swimming event would be considerably slower than the average speed during the running event, and the average speed during the running event would be considerably slower than the average speed during the bicycling event. In training for such a competition, the user could avail himself or herself of the interval training features of the device 10 by defining intervals according to speed and distance. For example, the user may define a first interval as speeds below 8 miles per hour (swimming); a second interval as speeds between eight miles per hour and 15 miles per hour (running); and a third interval as speeds over 15 miles per hour (bicycling). The user could further define subintervals according to distance, such as by dividing the swimming interval into three subintervals of 500 yards each; dividing the running interval into five subintervals of one mile each; and dividing the bicycling interval into three subintervals of five miles each. The device 10 would monitor the user's performance to automatically assign performance characteristics to the swimming, running, or bicycling interval and any subinterval the user may have created. During the training session the device 10 informs the user of performance relative to interval goals, and informs the user of changes in intervals and interval goals. After completing the training session the user could quickly review performance characteristics for each interval and subinterval and review historical and statistical analyses of the performance characteristics.

From the preceding description, it will be appreciated that the device of the present invention provides a number of substantial advantages over the prior art, including, for example, automatically tracking user performance, thereby eliminating the need for the user to manually measure performance during a training session or follow a pre-determined course. Furthermore, the device communicates goal and performance information to the user, helping the user reach pre-defined goals during the training session by informing the user of progress toward the goals. Additionally, the device communicates GPS-based navigation information to the user, enabling the user to visually monitor his or her location on a map or position on a course. Finally, the device automatically accumulates and stores performance statistics, eliminating the need for the user to manually record performance information and maintain the information for extended periods of time.

Although the invention has been described with reference to the preferred embodiments illustrated in the attached drawings, it is noted that equivalents may be employed and substitutions made herein without departing from the scope of the invention as recited in the claims. It will be appreciated, for example, that the housing and the attachment mechanism may take any practical functional, ergonomic, or aesthetically desirable shape.

The invention claimed is:

1. A method of aiding a user in reaching performance goals using a personal training device, the method comprising the steps of:
    (a) providing a user interface on the personal training device to receive course segment information from the user;
    (b) receiving goal information from the user through the user interface, the received goal information corresponding to one or more course segments associated with the course segment information;
    (c) storing the course segment information and the goal information in a memory associated with the personal training device;
    (d) determining, with a processor associated with the personal training device, performance information using geographic location information, timing information, and the course segment information;
    (e) comparing the performance information with the goal information using the processor; and (f) communicating training information to the user through the user interface, wherein the training information relates to both the goal information and the performance information.

2. The method as set forth in claim 1, further comprising the steps of:
   (a) storing the performance information in the memory; and
   (b) performing historical and statistical analyses on the performance information with the processor.

3. The method as set forth in claim 1, further comprising the steps of:
   (a) receiving performance threshold information from the user through the user interface; and
   (b) determining performance information with the processor using the performance threshold information.

4. The method as set forth in claim 3, wherein the performance threshold relates to a minimum speed.

5. The method as set forth in claim 3, further comprising the steps of:
   (a) pausing a timer function when a user is at a speed lower than the performance threshold; and
   (b) starting a timer function when a user is at a speed higher than the performance threshold.

6. A method of aiding a user in reaching performance goals using a personal training device, the method comprising the steps of:
   (a) providing a user interface on the personal training device to receive course segment information from the user;
   (b) receiving goal information from the user through the user interface, the received goal information corresponding to one or more course segments associated with the course segment information;
   (c) storing the course segment information and the goal information in a memory associated with the personal training device;
   (d) creating a virtual competitor with a processor associated with the personal training device, wherein the virtual competitor has a virtual performance relating to the goal information;
   (e) determining performance information with the processor using the course segment information;
   (f) comparing the performance information with the virtual performance using the processor; and
   (g) communicating training information to the user through the user interface, wherein the training information relates to both the virtual performance and the performance information.

7. A method of aiding a user in reaching performance goals using a personal training device, the method comprising the steps of:
   (a) providing a user interface on the personal training device to receive an input from the user indicating course segment information;
   (b) receiving goal information through the user interface, the received goal information corresponding to one or more course segments associated with the course segment information;
   (c) storing the course segment information and the goal information in a memory associated with the personal training device;
   (d) determining performance information using geographic location information and the course segment information with a processor associated with the personal training device;
   (e) comparing the performance information with the goal information using the processor; and
   (f) communicating training information to the user through the user interface, wherein the training information relates to both the goal information and the performance information.

8. The method as set forth in claim 7, wherein the training information includes a course segment transition.

9. The method as set forth in claim 7, further comprising the steps of:
   (a) storing the performance information in the memory;
   (b) performing historical and statistical analyses with the processor using the performance information and the course segment information; and
   (c) communicating historical and statistical information to the user through the user interface.

10. The method as set forth in claim 7, wherein the performance information is automatically stored at the completion of a course segment.

\* \* \* \* \*